United States Patent

Fuso et al.

Patent Number: 5,700,295
Date of Patent: Dec. 23, 1997

[54] UV ABSORBERS, THEIR PREPARATION AND THE USE THEREOF

[75] Inventors: Francesco Fuso, Therwil; Gerhard Reinert, Allschwil, both of Switzerland

[73] Assignee: Ciba Specialty Chemicals Corporation, Tarrytown, N.Y.

[21] Appl. No.: 541,007

[22] Filed: Oct. 11, 1995

[30] Foreign Application Priority Data

Oct. 13, 1994 [CH] Switzerland ............. 30880/94

[51] Int. Cl.$^6$ ............. D06M 13/358; C07D 251/52; C07D 239/48; C07D 239/50

[52] U.S. Cl. ............. 8/189; 544/194; 544/204; 544/209; 544/196; 544/198; 544/216; 544/217; 544/218; 544/299; 544/317; 544/323; 544/309; 544/311; 8/190; 8/127.6; 8/128.1; 8/128.3; 8/129; 8/155.59; 427/394

[58] Field of Search ............. 544/224, 295, 544/299, 301, 302, 303, 319, 320, 322, 326, 309, 311, 313, 314, 315, 316, 317, 318, 323, 324, 327, 328, 329, 333, 334, 335, 66, 68, 180, 190, 194, 204, 211, 212, 209, 196, 198, 216, 217, 218; 8/189, 190, 127.6, 128.1, 128.3, 129, 115.59, 684, 546, 549, 543; 427/394

[56] References Cited

U.S. PATENT DOCUMENTS

| | | |
|---|---|---|
| 3,041,330 | 6/1962 | Coleman et al. ............. 536/31 |
| 3,529,982 | 9/1970 | Luethi et al. . |
| 3,542,573 | 11/1970 | Biland et al. . |
| 3,661,606 | 5/1972 | Luethi et al. . |
| 3,906,033 | 9/1975 | Biland et al. . |
| 3,906,041 | 9/1975 | Hofer et al. . |
| 4,003,875 | 1/1977 | Lüthi et al. . |
| 5,336,800 | 8/1994 | Siegel et al. ............. 558/30 |

FOREIGN PATENT DOCUMENTS

| | | |
|---|---|---|
| 0388356 | 9/1990 | European Pat. Off. . |
| 388356 | 9/1990 | European Pat. Off. . |
| 3740650 | 6/1989 | Germany . |
| 03241069 | 10/1991 | Japan . |
| WO94/04515 | 3/1994 | WIPO . |

OTHER PUBLICATIONS

Chem. Abstract, vol. 111:235061 (1989) (Month Unknown).

*Primary Examiner*—Alan Diamond
*Attorney, Agent, or Firm*—Kevin T. Mansfield; David R. Crichton

[57] ABSTRACT

The invention relates to compounds of formula

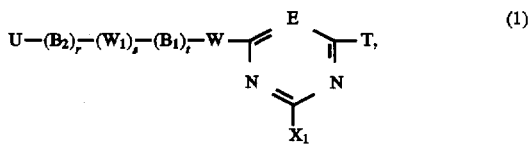

wherein the variables have the meanings given in the claims. The compounds are suitable for use as UV absorbers for the photochemical stabilisation of undyed, dyed or printed textile fiber materials and for enhancing the sun protection factor thereof.

14 Claims, No Drawings

UV ABSORBERS, THEIR PREPARATION AND THE USE THEREOF

The present invention relates to novel fibre-reactive UV absorbers, to a process for their preparation and to the use thereof for the photocemical stabilisation of undyed and dyed textile fibres and for enhancing the sun protection factor of such textile fibres.

That UV radiation is harmful to the skin is known. Protection against strong solar radiation is usually afforded by applying a composition that contains a UV absorber (sun cream) direct to the skin. In particularly sunny parts of the world, as in Australia and America, there has recently been a drastic increase in the incidence of skin damage induced by UV radiation. In these countries, increased attention is hence being paid to the problem of protecting the skin from solar radiation.

The proposal has been made not just to protect the skin direct, but also to provide clothing surrounding the skin as well as textile sun protective articles such as marquees or sunshades with additional protection against UV radiation. Most natural and synthetic textile fabrics, whether undyed or dyed, are usually at least partially permeable to UV radiation, so that the mere wearing of clothing does not afford adequate protection of the skin from damage induced by UV radiaton. Remedy is possible here by incorporating UV absorbers in textile fabric.

The results obtained in the field of textile materials, especially materials containing cellulosic fibres or natural or synthetic polyamide fibres, with respect to protection from UV radiation, have so far not been satisfactory, and there is a need to develop novel UV absorbers specially tailored to these materials.

Acccordingly, the invention relates to compounds of formula $$U-(B_2)_r-(W_1)_s-(B_1)_t-W-\underset{\underset{X_1}{N\diagdown\diagup N}}{\overset{E}{\diagup\diagdown}}T, \quad (1)$$

wherein

B$_1$ and B$_2$ are each independently of the other an aliphatic linking group,

U is the radical of a UV absorber selected from the group consisting of 2-hydroxybenzophenones, 2-hydroxyphenyl-1,3,5-triazines, oxamides, acrylates, unsubstituted or substituted benzoic acids and esters thereof, and radicals of formula $$(R)_{0-3}\diagup\hspace{-0.5em}\diagdown-M-\diagup\hspace{-0.5em}\diagdown R' \quad (1')$$

(R)$_{0-3}$ denotes 0 to 3 identical or different radicals R selected from the group consisting of sulfo, C$_1$–C$_4$alkyl, C$_1$–C$_4$alkoxy, halogen, hydroxy, carboxy, nitro and C$_1$–C$_4$alkylcarbonylamino, R' is hydrogen, sulfo, C$_1$–C$_4$alkyl or C$_1$–C$_4$alkoxy, M is a group —NR"—CO— or —NR"—SO$_2$—, R" is hydrogen or C$_1$–C$_4$alkyl, W is a group —NR$_2$—, —O— or —S—, R$_2$ is hydrogen or unsubstituted or substituted C$_1$–C$_4$alkyl, W$_1$ is a radical —C(O)O—, —O(O)C—, —C(O)NH— or —HN(O)C—, =E— is a group =N— or =C(T$_1$)—, and T$_1$ is halogen, C$_1$–C$_4$alkylsulfonyl, formyl, C$_2$–C$_4$alkoxycarbonyl or cyano, X$_1$ is halogen, hydroxy, sulfo, C$_1$–C$_4$alkylsulfonyl, phenylsulfonyl, unsubstituted or substituted amino, 3-carboxypyridin-1-yl or 3-carbamoylpyridin-1-yl, T independently has one of the meanings given for X$_1$ or is an alkoxy, aryloxy, alkylthio or arylthio radical which may be further substituted, or is a nitrogen-containing heterocyclic radical or is a reactive radical of formula $$-\underset{\underset{R_1}{|}}{N}-alk-SO_2-Y, \quad (2a)$$

$$-\underset{\underset{R_3}{|}}{N}-alk-W_2-alk'-SO_2-Y, \quad (2b)$$

$$-\underset{\underset{R_3}{|}}{N}-arylene-SO_2-Y, \quad (2c)$$

$$-\underset{\underset{R_3}{|}}{N}-arylene-(alk_u)-W_3-alk'-SO_2-Y \text{ or} \quad (2d)$$

$$-N\underset{\diagdown}{\diagup}\overset{\diagdown}{\diagup}N-alk-SO_2-Y, \quad (2e)$$

R$_1$ is hydrogen, C$_1$–C$_4$alkyl which is unsubstituted or substituted by hydroxy, sulfo, sulfato, carboxy or cyano, or is a radical $$-\underset{\underset{R_4}{|}}{alk}-SO_2-Y$$

R$_3$ is hydrogen or C$_1$–C$_4$alkyl,

R$_4$ is hydrogen, hydroxy, sulfo, sulfato, carboxy, cyano, halogen, C$_1$–C$_4$alkoxycarbonyl, C$_1$–C$_4$alkanoyloxy, carbamoyl or the group —SO$_2$—Y, alk and alk' are each independently of the other C$_1$–C$_6$alkylene, arylene is a phenylene or naphthylene radical which is unsubstituted or substituted by sulfo, carboxy, C$_1$–C$_4$alkyl, C$_1$–C$_4$alkoxy or halogen, Y is vinyl or a radical —CH$_2$—CH$_2$—Z and Z is a leaving group, W$_2$ is —O— or —NR$_3$—, W$_3$ is a group —SO$_2$—NR$_1$—, —CONR$_1$— or —NR$_1$CO—, and r, s, t and u are each independently of one another 0 or 1, s being 0 when t is 0, with the proviso that the compounds of formula (1) carry at least one sulfo or sulfato group and at least one group which is removable under alkaline conditions.

B$_1$ and B$_2$ defined as an aliphatic linking group may be straight-chain or branched C$_1$–C$_{12}$alkylene and, preferably, straight-chain or branched C$_1$–C$_6$alkylene. Illustrative examples of particularly preferred alkylene radicals B$_1$ and B$_2$ are methylene, 1,2-ethylene, 1,2-propylene, 1,3-propylene, 1,4-butylene, 2-methyl-1,5-pentylene and 1,6-hexylene. Methylene and 1,2-ethylene are preferred.

r and s are preferably each 0 and t is 0 or 1. r, s and t are most preferably each 0.

$R_2$ may be hydrogen or $C_1$-$C_4$alkyl which is unsubstituted or substituted by, typically, halogen, hydroxy, cyano, $C_1$-$C_4$alkoxy, $C_1$-$C_4$alkoxycarbonyl, carboxy, sulfamoyl, sulfo or sulfato. Preferably $R_2$ is hydrogen or $C_1$-$C_4$alkyl and, most preferably, is hydrogen, methyl or ethyl.

U defined as the radical of a 2-hydroxyphenyl-1,3,5-triazine is typically a radical of formula

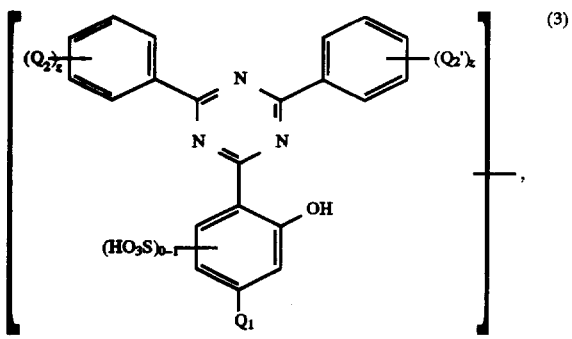

wherein z is an integer from 1 to 3, and $Q_1$, $Q_2$ and $Q_2'$ are each independently of one another hydrogen, hydroxyl, alkyl of 1 to 12 carbon atoms, alkoxy of 1 to 18 carbon atoms or unsubstituted or hydroxy-substituted $C_1$-$C_4$alkoxy-$C_1$-$C_4$alkoxy.

Illustrative examples of suitable 2-hydroxyphenyltriazine radicals U are the radical of 2,4,6-tris(2-hydroxy-4-octyloxyphenyl)-1,3,5-triazine, 2-(2-hydroxy-4-octyloxyphenyl)-4,6-bis(2,4-dimethylphenyl)1,3,5-triazine, 2-(2,4-dihydroxyphenyl)-4,6-bis(2,4-dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxypropoxy)phenyl]-4,6-bis(2,4-dimethylphenyl)-1,3,5-triazine, 2-(2-hydroxy-4-methoxy-6-sulfophenyl)-4,6-bis(phenyl)-1,3,5-triazine or 2-[2-hydroxy-4-(2-hydroxy-3-octyloxypropoxy)phenyl]-4,6-bis (2,4-dimethylphenyl)-1,3,5-triazine.

U as the radical of a 2-hydroxybenzophenone is conveniently a radical of formula

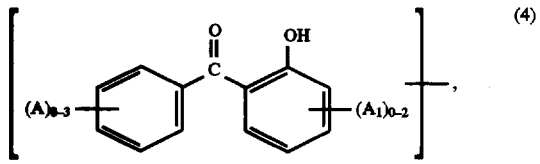

wherein $(A)_{0-3}$ is 0 to 3 identical or different radicals selected from the group consisting of halogen, hydroxyl, sulfo, $C_1$-$C_{12}$alkoxy or phenyl-$C_1$-$C_4$alkoxy, and $(A_1)_{0-2}$ is 0 to 2 identical or different selected from the group consisting of halogen, hydroxyl, sulfo, $C_1$-$C_{12}$alkoxy or phenyl-$C_1$-$C_4$alkoxy.

Illustrative examples of suitable 2-hydroxybenzophenone radicals U are the radical of 2,4-dihydroxybenzophenone, 2-hydroxy-4-methoxybenzophenone, 2-hydroxy-4-octyloxybenzophenone, 2-hydroxy-4-decyloxybenzophenone, 2-hydroxy-4-dodecyloxybenzophenone, 2-hydroxy-4-methoxy-5-sulfobenzophenone, 2-hydroxy-4-benzyloxybenzophenone, 4,2',4'-trihydroxybenzophenone or 2'-hydroxy-4,4'-dimethoxybenzophenone.

U as the radical of a 2-hydroxybenzophenone is preferably a radical of formula

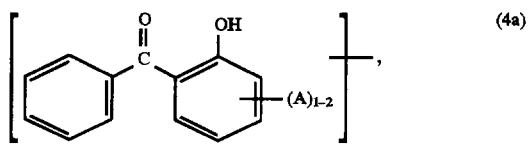

wherein $(A)_{1-2}$ is 1 or 2 identical or different radicals selected from the group consisting of $C_1$-$C_{12}$alkoxy and sulfo.

U as the radical of an oxamide is conveniently an oxalanilide radical of formula

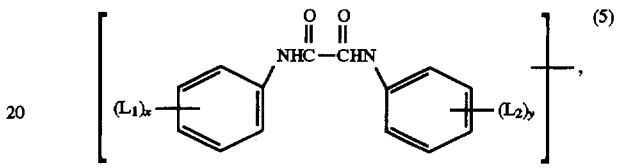

wherein $(L_1)_x$ denotes x identical or different substituents $L_1$ selected from the group consisting of sulfo, hydroxy, alkyl, alkoxy or alkylthio, each of 1 to 22 carbon atoms and each unsubstituted or substituted in the alkyl moiety by sulfo, or phenoxy or phenylthio, each unsubstituted or substituted in the phenyl ring by sulfo, $(L_2)_y$ denotes y identical or different substituents $L_2$ selected from the group consisting of sulfo, alkyl, alkoxy or alkylthio, each of 1 to 22 carbon atoms and each unsubstituted or substituted in the alkyl moiety by sulfo, or phenoxy or phenylthio, each unsubstituted or substituted in the phenyl ring by sulfo, and x and y are each independently of the other an integer from 0 to 3, the sum of (x+y) being $\geq 1$.

x is preferably 1, 2 or 3 and, most preferably, 1 or 2. y is preferably 0 or 1 and, most preferably, 0. The substituents $L_1$ and $L_2$ are each independently of the other preferably sulfo, $C_1$-$C_4$alkyl or $C_1$-$C_{12}$alkoxy and, most preferably, sulfo or $C_1$-$C_4$alkoxy.

Typical examples of suitable oxalanilide radicals U are the radical of 4,4'-dioctyloxyoxanilide, 2,2'-diethoxyoxanilide, 2,2'-dioctyloxy-5,5'-di-tert-butyloxanilide, 2,2'-di-dodecyloxy-5,5'di-tert-butyloxanilide, 2-ethoxy-2'-ethyloxanilide, 2-methoxy-5-sulfooxanilide, 2-ethoxy-5-sulfooxanilide, 2,5-dimethoxyoxanilide, 2-ethoxy-5-tert-butyl-2'-ethyloxanilide, alone or in admixture with the radical of 2-ethoxy-2'-ethyl-5,4'-di-tert-butyl-oxanilide, or mixtures of the radicals of o- and p-methoxyanilides and of o- and p-diethoxyoxanilides.

U as oxamide is preferably a radical of formula

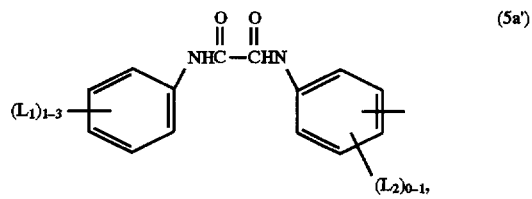

wherein $(L_1)_{1-3}$ is 1 to 3 identical or different radicals $L_1$ selected from the group consisting of sulfo, hydroxy, $C_1$-$C_4$alkyl and $C_1$-$C_{12}$alkoxy, and $(L_2)_{0-1}$ is 0 to 1 sbstituents $L_2$ selected from the group consisting of sulfo, $C_1$-$C_4$alkyl and $C_1$-$C_{12}$alkoxy.

U as oxamide is preferably a radical of formula

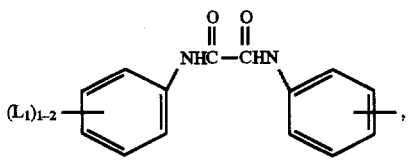   (5a)

worin $(L_1)_{1-2}$ is 1 or 2 radicals L selected from the group consisting of sulfo, hydroxy, $C_1$–$C_4$alkyl and $C_1$–$C_{12}$alkoxy, preferably sulfo and $C_1$–$C_4$alkoxy.

Suitable acrylate radicals U are $C_1$–$C_{10}$alkylacrylates which in α-position are unsubstituted or substituted by cyano or carbo-$C_1$–$C_4$alkoxy, in one β-position carry a phenyl, $C_1$–$C_4$alkoxyphenyl or indolinyl radical, and in the other β-position are unsubstituted or substituted by phenyl, $C_1$–$C_4$alkoxyphenyl or $C_1$–$C_4$alkyl.

Typical examples of acrylate radicals U are the radical of ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-β-cyanovinyl)-2-methylindoline.

U as the radical of an unsubstituted or substituted benzoic acid or an ester thereof is typically a benzoic acid radical which is unsubstituted or substituted by hydroxy or $C_1$–$C_4$alkyl or the phenyl, $C_1$–$C_8$alkylphenyl or $C_1$–$C_{18}$alkyl ester thereof. Illustrative examples are the radical of benzoic acid, 4-tert-butylphenylsalicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, or 2-methyl-4,6-di-tert-butylphenyl 3,5-di-tert-butyl-4-hydroxybenzoate.

When U is a radical of formula (1') above, then $(R)_{0-3}$ preferably denotes 0 to 3 identical or different radicals R selected from the group consisting of sulfo, methyl, methoxy, hydroxy and carboxy, R' is preferably hydrogen and M is preferably a group —NH—CO— or NH—SO$_2$—. U is in this case preferably a radical of formula

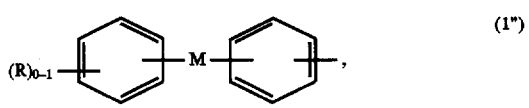   (1")

wherein $(R)_{0-1}$ is 0 or 1 radical R selected from the group consisting of sulfo, methyl, methoxy, hydroxy and carboxy, and M is preferably a group —NH—CO— or NH—SO$_2$—.

U is preferably a radical of formula (1"), (4a) or (5a') above or a benzoic acid radical which is unsubstituted or substituted by hydroxy or $C_1$–$C_4$alkyl or the phenyl, $C_1$–$C_8$alkylphenyl or $C_1$–$C_{18}$alkyl ester thereof and, most preferably, a radical of formula (5a) above.

W is preferably a —NR$_2$— radical, wherein R$_2$ has the meanings and preferred meanings given above. The particularly preferred meaning of W is —NH—.

X$_1$ defined in formula (1) as unsubstituted or substituted amino will be typically understood as meaning —NH$_2$, N-mono- or N,N-di-$C_1$–$C_4$alkylamino, each unsubstituted or substituted in the alkyl moiety by hydroxy, carboxy, sulfo, sulfato or $C_1$–$C_4$alkoxy; cyclohexylamino; or phenylamino or N-$C_1$–$C_4$alkyl-N-phenylamino, each unsubstituted or substituted in the phenyl moiety by $C_1$–$C_4$alkyl, $C_1$–$C_4$alkoxy, carboxy, sulfo, halogen or by a radical of formula —SO$_2$—Y   (6a)

—CONH—(CH$_2$)$_p$—SO$_2$—Y   (6b)

wherein Y is as previously defined and p is an integer from 1 to 6, substituted phenylamino or N-$C_1$–$C_4$alkyl-N-phenylamino or 1- or 2-naphthylamino which is substituted by one or more than one sulfo group.

In formula (6b), p is preferably 2, 3 or 4 and, most preferably, 2 or 3.

X$_1$ defined as unsubstituted or substituted amino is preferably amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, or phenylamino which is substituted by a radical of formula (6a) or (6b). Most preferably, X$_1$ as unsubstituted or substituted amino is amino, β-sulfoethylamino, β-hydroxyethylamino, N,N-di-β-hydroxyethylamino and o-, m- or p-sulfophenylamino.

Preferred meanings of X$_1$ are chloro, fluoro, hydroxy, amino, N-mono- or N,N-di-$C_1$–$C_4$alkylamino, each unsubstituted or substituted in the alkyl moiety by hydroxy, sulfo or sulfato, or phenylamino which is unsubstituted or substituted in the phenyl moiety by methyl, ethyl, methoxy, ethoxy, carboxy, sulfo, chloro or by a radical of formula (6a) or (6b).

Most preferably, X$_1$ is chloro or fluoro.

Where the variable =E— is a group =C(T$_1$)—, T$_1$ is preferably halogen and, most preferably, fluoro or chloro. The variable =E— is preferably the group =N—.

T in the significance of an alkoxy radical is preferably a $C_1$–$C_4$alkoxy radical, typically methoxy, ethoxy, n- or isopropoxy or n-, iso-, sec- or tert-butoxy. The preferred meanings are methoxy and isopropoxy.

T in the significance of an aryloxy radical is typically unsubstituted or substituted phenoxy, possible substituents being $C_1$–$C_4$alkyl, $C_1$–$C_4$alkoxy, halogen, hydroxy, carboxy or sulfo.

T defined as an alkylthio radical is typically $C_1$–$C_4$alkylthio and, preferably, methylthio or ethylthio.

T defined as an arylthio radical is typically unsubstituted or substituted phenylthio, possible substituents being $C_1$–$C_4$alkyl, $C_1$–$C_4$alkoxy, halogen, hydroxy, carboxy or sulfo.

If T independently has one of the meanings previously given for X$_1$, then the preferred meanings will also in this case apply.

T in the significance of a nitrogen-containing heterocyclic radical will typically be the piperidino or piperazino radical or, preferably, the morpholino radical.

Suitable leaving groups Z are typically —Cl, —Br, —F, —OSO$_3$H, —SSO$_3$H, —OCO—CH$_3$, —OPO$_3$H$_2$, —OCO—CCl$_3$, —OCO—CHCl$_2$, —OCO—CH$_2$Cl, —OSO$_2$—$C_1$–$C_4$alkyl, —OSO$_2$—N($C_1$–$C_4$alkyl)$_2$ or —OCO—C$_6$H$_5$.

Preferably Z is a group of formula —Cl, —OSO$_3$H, —SSO$_3$H, —OCO—CH$_3$, —OCO—C$_6$H$_5$ or —OPO$_3$H$_2$, preferably —Cl or —OSO$_3$H, most preferably —OSO$_3$H.

Y is preferably vinyl, β-chloroethyl, β-sulfatoethyl, β-thiosulfatoethyl, β-acetoxyethyl, β-phenoxyethyl or β-phosphatoethyl and, most preferably β-sulfatoethyl or vinyl.

alk and alk' are each independently of the other typically a methylene, ethylene, 1,3-propylene, 1,4-butylene, 1,5-pentylene or 1,6-hexylene radical or the branched isomers thereof.

Preferably alk and alk' are each independently of the other a $C_1$–$C_4$alkylene radical and, most preferably, an ethylene radical or a 1,2- or 1,3-propylene radical.

arylene is preferably a 1,3- or 1,4-phenylene radical which is unsubstituted or substituted by sulfo, methyl, methoxy or carboxy or an unsubstituted or sulfo-substituted naphthylene radical and, most preferably, an unsubstituted 1,3- or 1,4-phenylene radical.

$R_1$ is preferably hydrogen or $C_1$–$C_4$alkyl such as methyl, ethyl, propyl, isopropyl, butyl, isobutyl, sec-butyl or tert-butyl. Most preferably $R_1$ is hydrogen.

$R_3$ is preferably hydrogen, methyl or ethyl, most preferably hydrogen.

$R_4$ is preferably hydrogen.

$W_2$ is preferably —NH— or —O— and, most preferably, —O—.

$W_3$ is preferably a group of formula —CONH— or —NHCO—, most preferably a group of formula —CONH—.

u is preferably 0.

A reactive radical T is preferably a radical of formulae (2a) to (2e) above, wherein $W_3$ is a group of formula —CONH— or —NHCO—, $R_1$, $R_3$ and $R_4$ are each hydrogen, $W_2$ is —O— or —NH—, alk and alk' are each independently of the other ethylene or propylene, arylene is phenylene which is unsubstituted or substituted by methyl, methoxy, carboxy or sulfo, or naphthylene which is unsubstituted or substituted by sulfo, Y is vinyl or β-sulfatoethyl and u is 0.

Particularly preferred fibre-reactive radicals T are those of formula

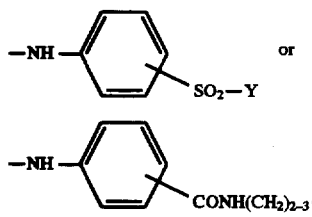

wherein Y is vinyl or β-sulfatoethyl.

A preferred embodiment of this invention relates to compounds of formula

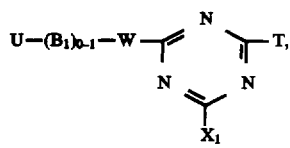

wherein $B_1$ is straight-chain or branched $C_1$–$C_6$alkylene, W is —NH—, $X_1$ is chloro or fluoro, U is (i) a radical of formula

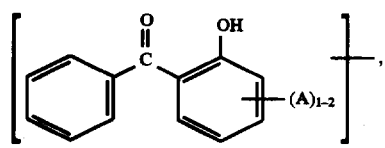

wherein $(A)_{1-2}$ is 1 or 2 identical or different radicals selected from the group consisting of $C_1$–$C_{12}$alkoxy and sulfo; or (ii) a radical of formula

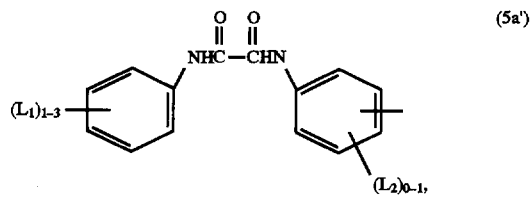

wherein $(L_1)_{1-3}$ is 1 to 3 radicals $L_1$ selected from the group consisting of sulfo, hydroxy, $C_1$–$C_4$alkyl and $C_1$–$C_{12}$alkoxy and $(L_2)_{0-1}$ is 0 to 1 substituents $L_2$ selected from the group consisting of sulfo, $C_1$–$C_4$alkyl and $C_1$–$C_{12}$alkoxy; or (iii) an unsubstituted or hydroxy- or $C_1$–$C_4$alkyl-substituted benzoic acid radical or the phenyl, $C_1$–$C_8$alkylphenyl or $C_1$–$C_{18}$alkyl ester thereof; or (iv) a radical of formula

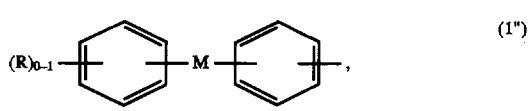

wherein $(R)_{0-1}$ is 0 or 1 radical R selected from the group consisting of sulfo, methyl, methoxy, hydroxy and carboxy, and M is a group —NH—CO— or NH—$SO_2$—, and T is amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, mono-, di- or trisulfonaphthylamino, morpholino or a radical of formulae (2a) to (2e) previously shown above, wherein $W_3$ is a group of formula —CONH— or —NHCO—, $R_1$, $R_3$ and $R_4$ are each hydrogen, $W_2$ is —O— or —NH—, alk and alk' are each independently of the other ethylene or propylene, arylene is phenylene which is unsubstituted or substituted by methyl, methoxy, carboxy or sulfo, or naphthylene which is unsubstituted or substituted by sulfo, Y is vinyl or β-sulfatoethyl, and u is 0.

A particularly preferred embodiment of the invention relates to compounds of formula (1a) shown above, wherein U is a radical of formula (5a') or, preferably, (5a) shown above.

Particularly interesting compounds are those of formula

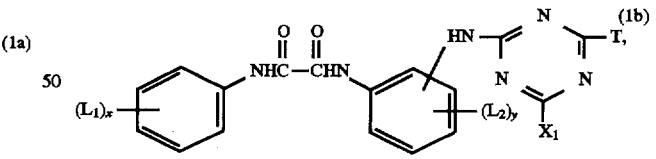

wherein $(L_1)_x$, $(L_2)_y$, T and $X_1$ each have the meanings and preferred meanings given above.

In formulae (1) to (6b), $C_1$–$C_{18}$alkyl will typically be methyl, ethyl, n- or isopropyl, n-, iso-, sec- or tert-butyl or straight-chain or branched heptyl, octyl, nonyl, decyl, undecyl, dodecyl, tridecyl, tetradecyl, pentadecyl, hexadecyl, heptadecyl or octadecyl.

$C_1$–$C_{18}$Alkoxy will typically be taken to mean methoxy, ethoxy, n- or isopropoxy, n-, iso-, sec- or tert-butoxy or or straight-chain or branched pentoxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy or octadecyloxy. $C_1$–$C_{12}$Alkylene is typically methylene, 1,1- or 1,2-ethylene, 1,2- or 1,3-propylene or straight-chain or branched butylene, pentylene, hexylene, heptylene, octylene, nonylene, decylene, undecylene or dodecylene. Halogen will be typically understood as meaning fluoro, chloro or bromo. $C_1$–$C_4$Alkoxycarbonyl will typically be taken to mean methoxycarbonyl, ethoxycarbonyl, n- or isopropoxycarbonyl or n-, iso-, sec- or tert-butoxycarbonyl. $C_1$–$C_4$Alkylthio is exemplified by methylthio or ethylthio. $C_5$–$C_8$Cycloalkyl is typically cyclopentyl or, preferably, cyclohexyl.

The compounds of formula (1) must carry at least one group which is removable with alkali, i.e. they carry at least one halogen atom at a triazinyl radical or a radical of formula (2a) to (2e) or (6a) or (6b) above.

The compounds of formula (1) must further carry at least one sulfo or sulfato group, in which case these compounds can be obtained in the form of the free acid or, preferably, in salt form, typically as sodium, lithium, potassium or ammonium salt.

The compounds of formula (1) are fibre-reactive. By fibre-reactive radicals are meant those radicals that are able to react with the hydroxyl groups of cellulose, with the amino, carboxyl, hydroxyl and thiol groups of wool and silk, or with the amino and, where present, carboxyl groups of synthetic polyamides to form covalent chemical bonds.

The compounds of formula (1) may conveniently be prepared by reacting a compound of formula $$U—(B_2)_r—(W_1)_s—(B_1)_t—W—H \quad (7)$$

a compound of formula $$Hal—\overset{E}{\underset{N\underset{X_1}{\diagdown}N}{\diagup}}—Hal, \quad (8)$$

and a compound of formula $$T^*—H \quad (9)$$

wherein U, $B_1$, $B_2$, W, $W_1$, E, $X_1$, r, s and t are each as previously defined, Hal is halogen, preferably fluoro or chloro, and T* has the meaning previously given for T, except halogen, with one another, and the sequence of the partial reactions may be freely chosen having regard to the starting compounds.

A preferred variant of the process consists in reacting c. 1 molar equivalent of a compound of formula (7) with c. 1 molar equivalent of a compound of formula $$Hal—\overset{E}{\underset{N\underset{X_1}{\diagdown}N}{\diagup}}—T \quad (8a)$$

wherein Hal, E, $X_1$ and T each have the meanings previously assigned to them.

The conditions to be used in the condensation of the compounds of formula (7), (8) and (9) are well known in the field of the chemistry of reactive dyes. This reaction is usually carried out in aqueous or aqueous-organic medium in the presence of an acid acceptor, conveniently sodium carbonate or sodium hydroxide.

The compounds of formulae (8), (8a) and (9) are known or can be obtained by per se known methods.

Some of the UV absorbers of formula (7) belong to known classes of compounds and can be prepared in per se known manner, as disclosed, inter alia, in U.S. Pat. No. 3,041,330, U.S. Pat. No. 3,042,669 or U.S. Pat. No. 3,159,646.

The compounds of formula (7a)

wherein $(L_1)_x$ and $(L_2)_y$ each have the meanings and peferred meanings previously assigned to them, are novel and are likewise a further object of the invention. They may conveniently be prepared by reacting a nitrooxanilic acid derivative of formula wherein D may be halogen or $C_1$–$C_4$alkoxy, and $(L_2)_y$ is as previously defined, with an aniline derivative of formula wherein $(L_1)_x$ is as previously defined, and subsequently hydrogenating the resultant nitrooxanilide compound catalytically to the corresponding amino compound.

The novel UV absorbers of formula (1) are suitable for the photochemical stabilisation of undyed and dyed or printed fibre materials, typically of silk, leather, wool, polyamide or polyurethanes, and, in particular, of cellulosic fibre materials of all kinds. Such fibre materials are typically the natural cellulose fibres such as cotton, linen, jute and hemp, as well as cellulose and regenerated cellulose. Cotton textile fabrics are preferred. The compounds of formula (1) are also suitable for the photochemical stabilisation of hydroxyl group-containing fibres that are components of fibre blends, e.g. blends of cotton and polyester or polyamide fibres.. A further preferred field of use relates to the blocking or lessening of UV radiation passing through said textile fabrics (UV cutting) and the increased sun protection that textile fabrics treated with a compound of this invention afford the human skin.

This end is achieved by applying one or more than one compound of formula (1), advantageously in an amount of 0.01 to 5% by weight, preferably 0.1 to 3% by weight and, most preferably, 0.25 to 2% by weight, based on the weight of the fibre material, to the textile material by a conventional dyeing process for reactive dyes. If the textile fabric is a cellulosic material dyed with a reactive dye, then the UV absorber of formula (1) can be applied before, during or after dyeing, preferably simultaneously with the application of the dye.

The compounds of formula (1) can be applied to the fibre material and fixed thereon in different manner, preferably in the form of aqueous solutions or print pastes. They are suitable for the exhaust process as well as for pad dyeing. They can be used at low temperature and require only short steaming times in pad-steam processes. Fixation is excellent and non-fixed absorber can be easily washed off, the difference between degree of exhaustion and percentage fixation being remarkably small. The compounds of formula (1) are also suitable for printing, especially on cotton.

The textile materials treated with the compounds of formula (1) have enhanced protection against photochemical fibre degradation and yellowing as well as, in the case of dyed material, enhanced fastness to hot light. The strongly enhanced light stability of the treated textile fabric is to be particularly highlighted and, in particular, the good protective action against short-wave UV-B radiation. This effect is seen in the fact that, compared wth untreated fabric, textile fabric treated with a compound of formula (1) has a greatly enhanced sun protection factor (SPR).

The sun protection factor is defined as the quotient of harmful UV radiation without sun protection and harmful UV radiation with sun protection. Accordingly, a sun protection factor is also an indicator of the permeability of the untreated fabric and the fabric treated with a compound of formula (1) to UV radiation. The calculation of the sun protection factor of textile fabrics is explained, inter alia, in WO 94/04515 or in J. Soc. Cosmet. Chem. 40, 127–133 (1989) and can be determined in analogous manner.

The compounds of this invention have the further advantage that they do not stain the textile material when used for obtaining an appropriate finish.

The invention is illustrated by the following Examples in which parts and percentages are by weight, unless otherwise indicated.

EXAMPLE 1

A mixture of 20 parts of ethyl 3-nitrooxanilate and 23 parts of o-phenetidine is heated for 4 hours under nitrogen to 140°–150° C. The pressure is then lowered to c. 40 mbar and the mixture is stirred for 4 hours at c. 140° C., cooled, and the semi-solid residue is washed with water and 4N hydrochloric acid. The compound of formula

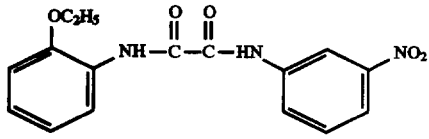
(10)

is isolated by filtration, washed with water and dried.

EXAMPLE 1a

The procedure as described in Example 1 is repeated, using 51.9 parts instead of 23 parts of o-phenetidine, and using 45 parts instead of 20 parts of ethyl 4-nitrooxanilate, to give the compound of formula

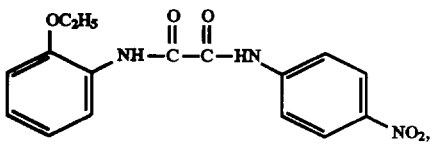
(10a)

EXAMPLE 2

9.9 parts of the compound of formula (10) obtained in Example 1 are added to 55 parts of 100% sulfuric acid over 1 hour, while keeping the temperature below 20° C. The reaction mixture is then stirred for 1 hour and poured on ice. After addition of sodium chloride, the precipitated solid is isolated by filtration, taken up in sodium chloride solution, and reprecipitated by treatment with sodium hydroxide solution, giving the product of formula

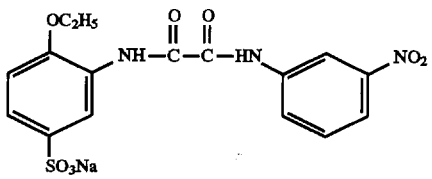

EXAMPLE 2a

The procedure as described in Example 2 is repeated, replacing the compound of formula (10) with the equivalent amount of the compound of formula (10a) to give the compound of formula

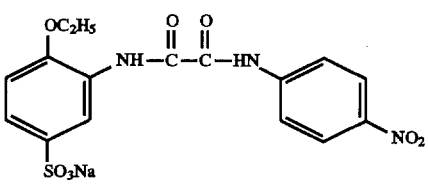

EXAMPLE 3

A suspension of 12 parts of the nitro compound obtained in Example 2 is catalytically hydrogenated in 1000 ml of water using a Pd/C (5%) catalyst. The resultant amino compound of formula

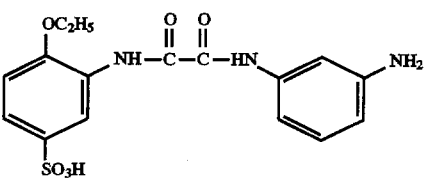

is isolated and purified in conventional manner.

EXAMPLE 3a

In general accordance with the procedure described in Example 3, the compound of formula

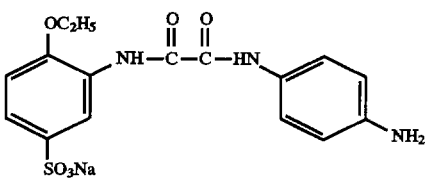

can be prepared from the nitro compound obtained in Example 2a.

EXAMPLES 3b–3i

The following oxanilide intermediates can be prepared in general accordance with the procedures described in Examples 1 to 3a:

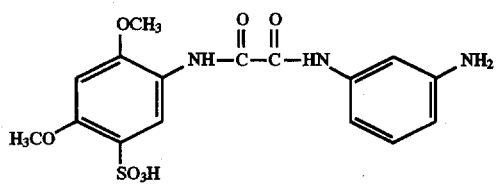
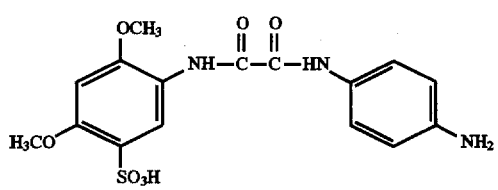
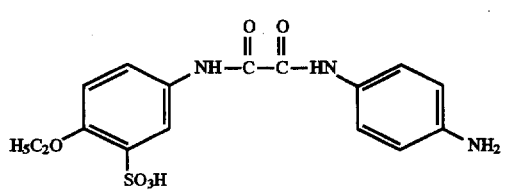
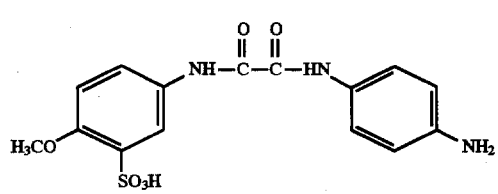
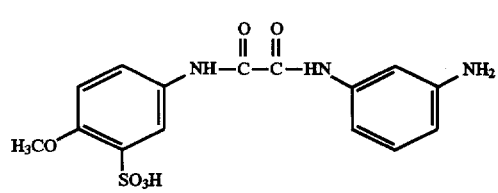
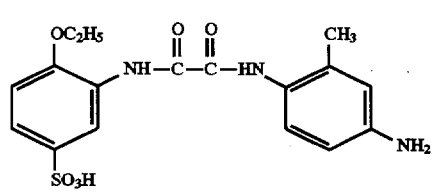
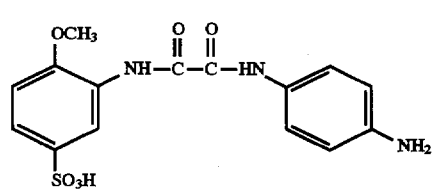
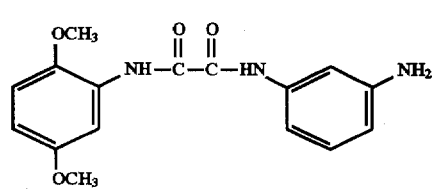

EXAMPLE 3j

A solution of 28.5 parts of ethyl 2-ethoxyoxanilate in 56 parts of N,N-dimethylacetamide are added at 40° C., under nitrogen, to a mixture of 22.5 parts of 1,4-phenylenediamine-2-sulfonic acid (as sodium salt) and 9.5 parts of imidazole in 56 parts of N,N-dimethylacetamide. The reaction mixture is stirred for c. 18 hours at 90° C., then cooled to 45° C., and 220 parts of water are added. The product of formula

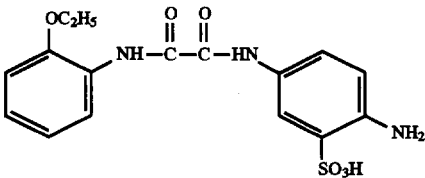

is isolated by filtration, washed with water and dried.

EXAMPLE 3k 10 parts of the compound obtained in Example 3j are added to 50 parts of 100% sulfuric acid over 15 minutes, while keeping the temperature at c. 20° C. The reaction mixture is then stirred for 1 hour at room temperature and then poured on ice. After addition of sodium chloride, the precipitated solid is isolated by filtration and taken up in sodium chloride solution. The compound of formula

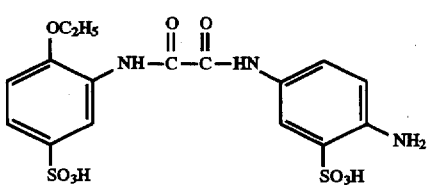

is isolated as sodium salt by treatment with sodium hydroxide solution.

EXAMPLES 3l to 3r

The following oxanilide intermediates can also be prepared as described in Examples 3j and 3k:

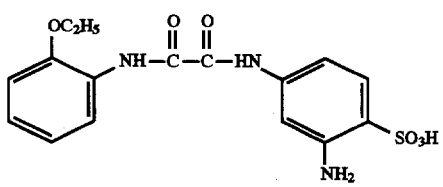

3l

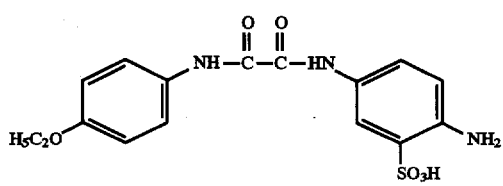

3m

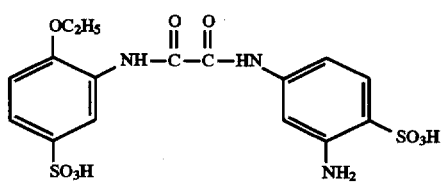

3n

-continued

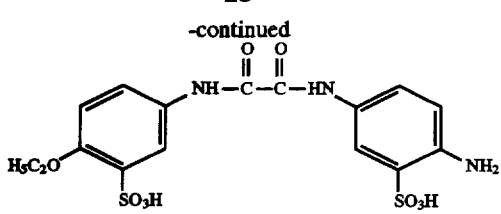
3o

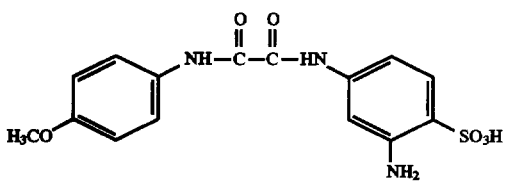
3p

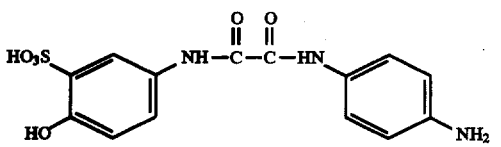
3q

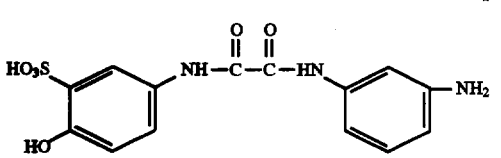
3r

EXAMPLE 4

An aqueous suspension of 3.79 parts of the amino compound obtained in Example 3 is added to an ice-cold aqueous suspension of the condensate of 1.84 parts of cyanuric chloride and 2.81 parts of 4-β-sulfatoethylsulfonylaniline (preparation as described in DE-A 3 740 650). The temperature is raised to 35° C. and the reaction mixture is stirred until the condensation is complete, while keeping the pH constant at 7 by the dropwise addition of 15% sodium carbonate solution. The product is thereafter salted out in conventional manner, isolated by filtration, washed with sodium chloride solution and dried, giving the compound of formula

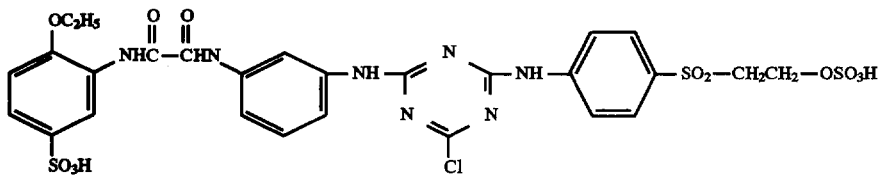

as a powder. Application of this compound to cotton fabric by a standard method of dyeing with reactive dyes gives a greatly enhanced sun protection factor compared with untreated fabric.

EXAMPLE 4a

In general accordance with the procedure described in Example 4, the compound of formula

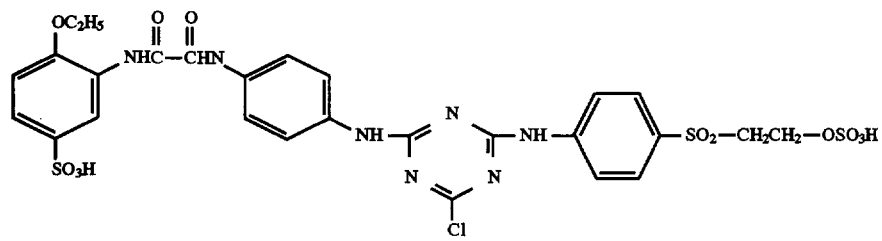

can be prepared from 7.6 parts of the amino compound obtained in Example 3a and 8.6 parts of the condensate of cyanuric chloride and 4-β-sulfatoethylsulfonylaniline described in Example 4. Application of this compound to cotton fabric by a standard method of dyeing with reactive dyes gives a greatly enhanced sun protection factor compared with untreated fabric.

EXAMPLES 5–13

The compounds of formula

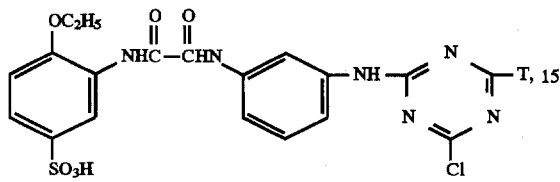

wherein T has the meanings given in the Table, can be prepared in general accordance with the procedures described in Examples 1, 2, 3 and 4. When applied to cotton, these compounds impart a sun protection factor comparable to that obtained with the compound of Example 4.

| Examples | T |
|---|---|
| 5 | 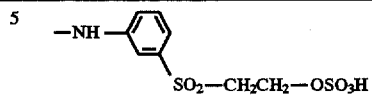
$SO_2-CH_2CH_2-OSO_3H$ |
| 6 | 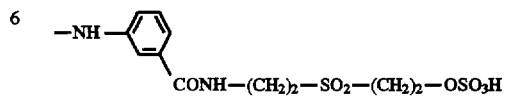
$CONH-(CH_2)_2-SO_2-(CH_2)_2-OSO_3H$ |
| 7 | $-NH-$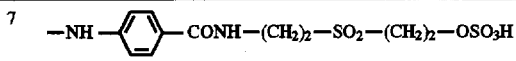$-CONH-(CH_2)_2-SO_2-(CH_2)_2-OSO_3H$ |
| 8 | $-NH-(CH_2)_2-O-(CH_2)_2-SO_2-CH=CH_2$ |
| 9 | $-NH-(CH_2)_2-SO_2-CH_2-CH_2-Cl$ |
| 10 | 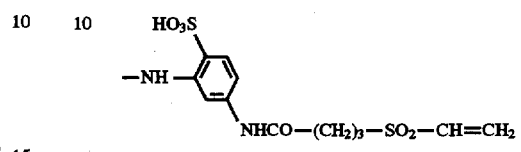 |
| 11 | 
$SO_3H$ ... $SO_2-CH_2CH_2-OSO_3H$ |
| 12 | $-NH-$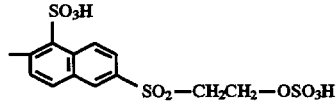
$SO_3H$ |
| 13 | $-NH-$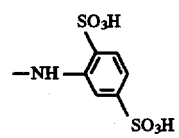
$SO_3H$, $SO_3H$ |

EXAMPLES 14–38b

Following the procedure of Example 4, the following compounds can be prepared from the intermediates obtained according to Examples 3 to 3r. Application of these compounds to cotton fabric by a standard method of dyeing with reactive dyes gives a greatly enhanced sun protection factor compared with untreated fabric.

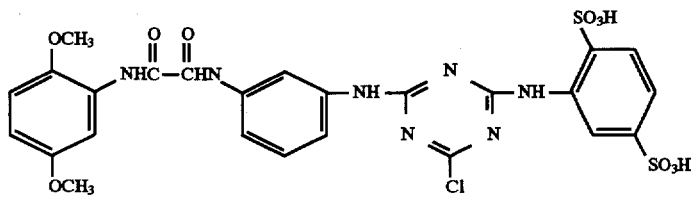

14

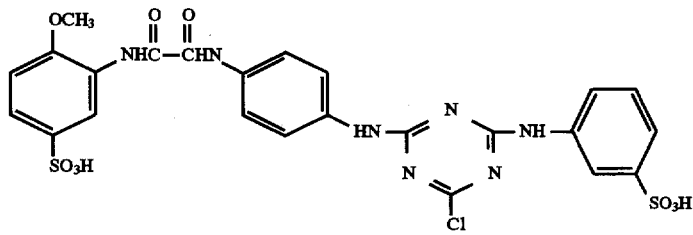

15

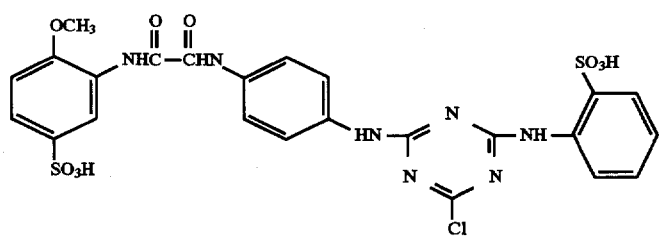

16

17
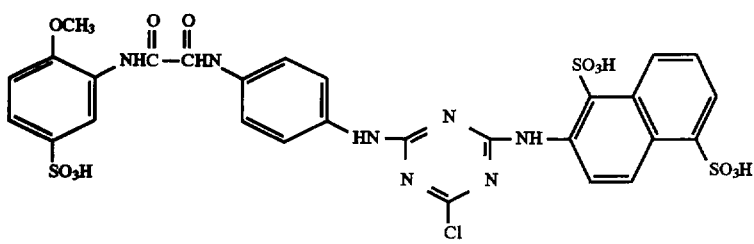
18
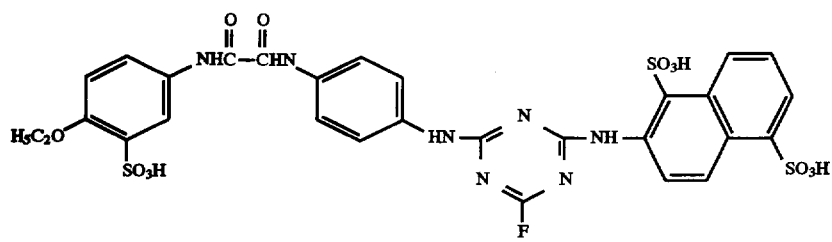
19
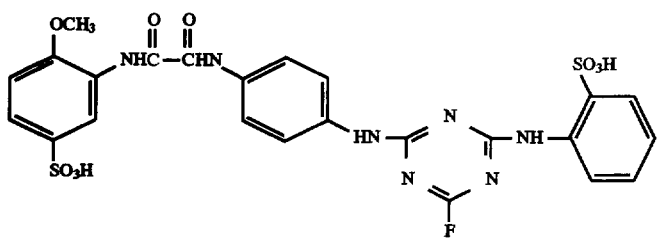
20
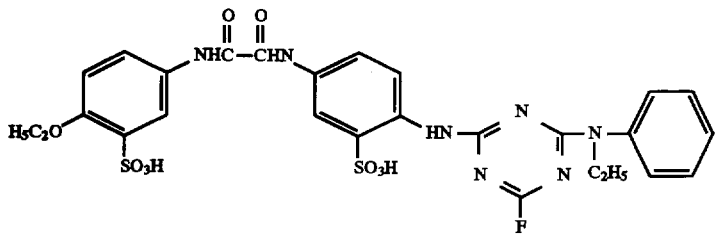
21
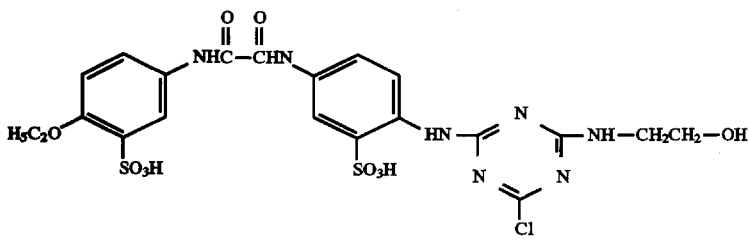
22
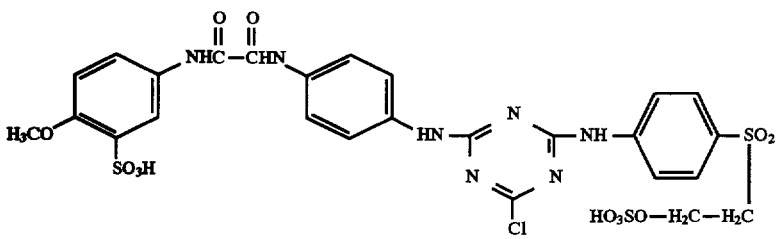

-continued
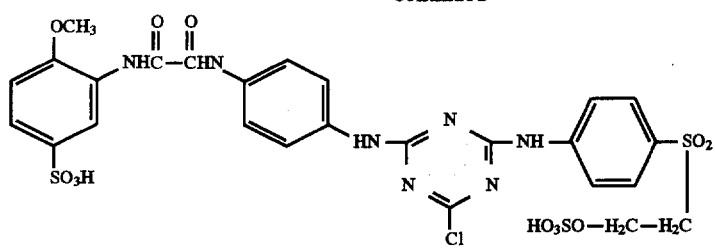
23
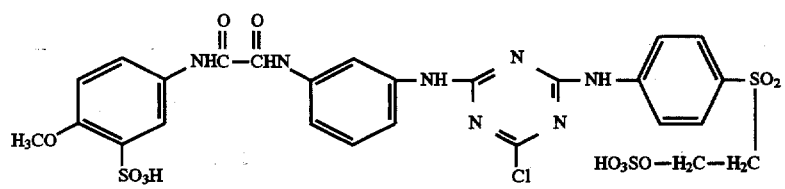
24
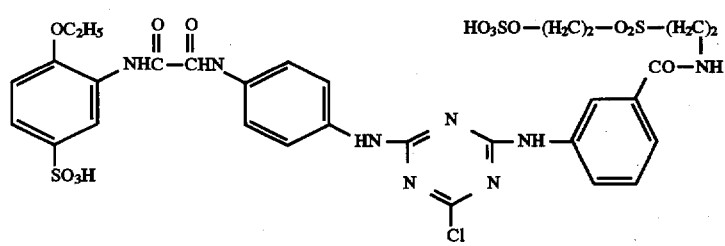
25
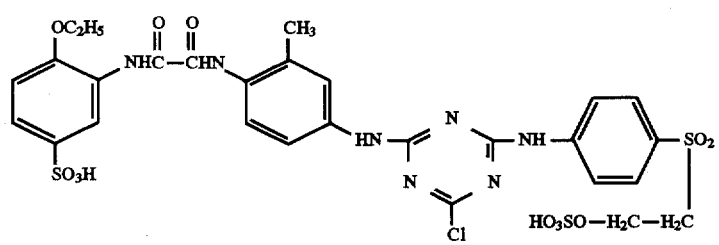
26
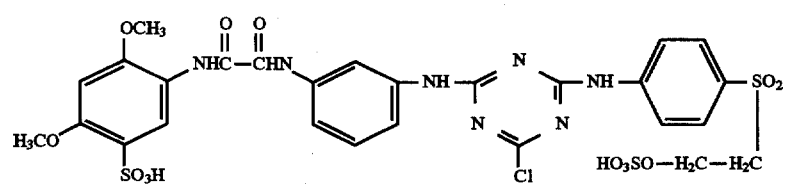
27
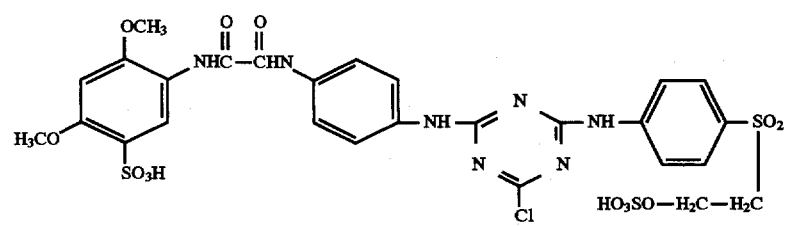
28
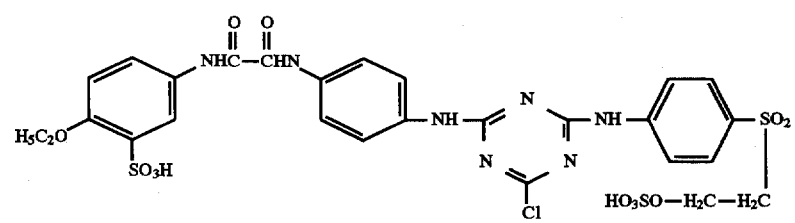
29

30
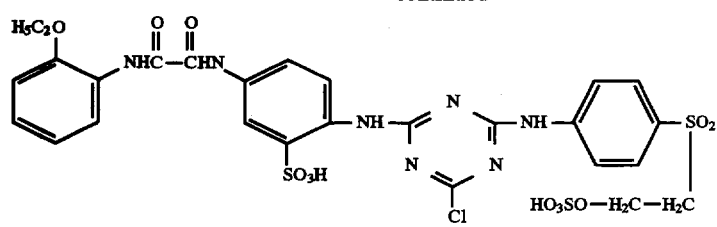
31
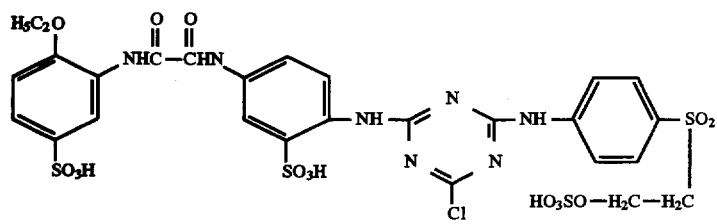
32
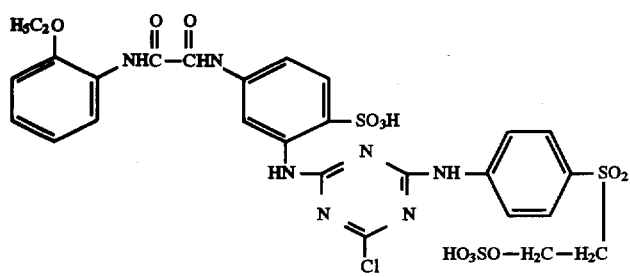
33
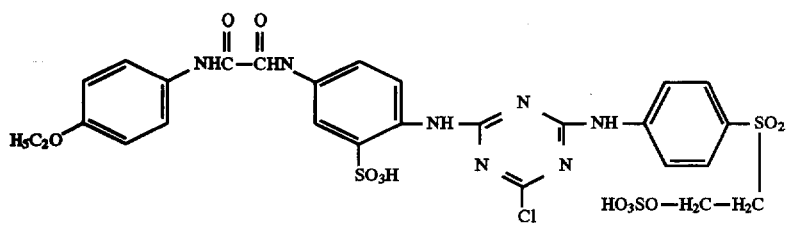
34
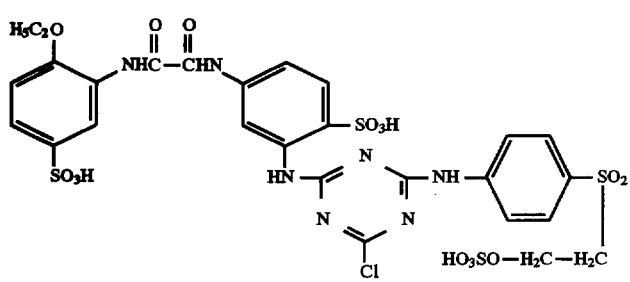
35
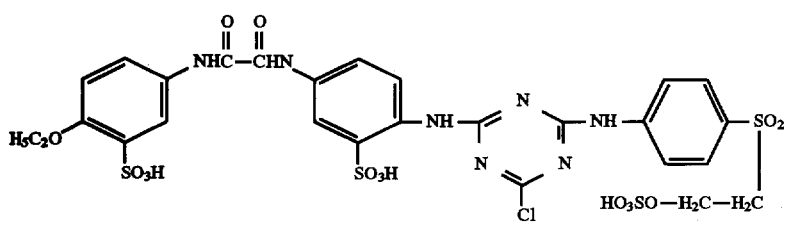

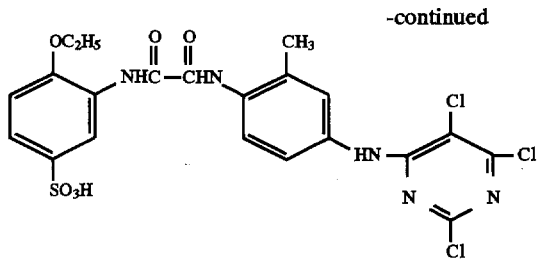

36

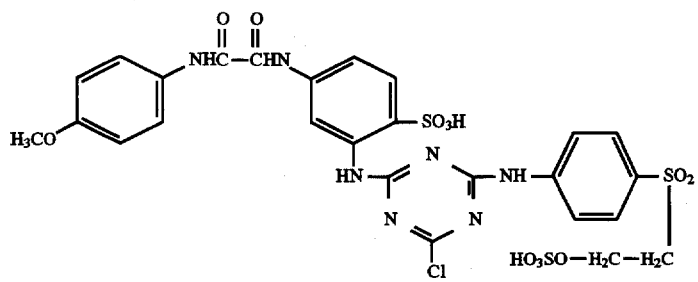

37

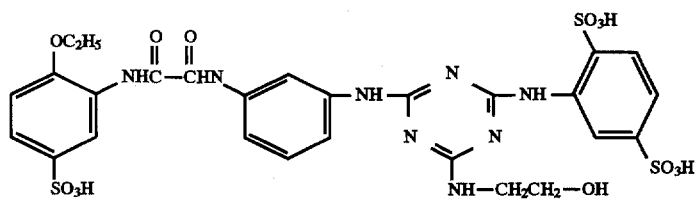

38

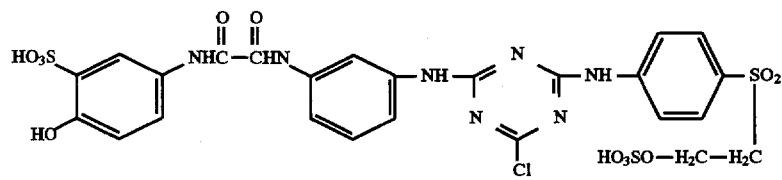

38a

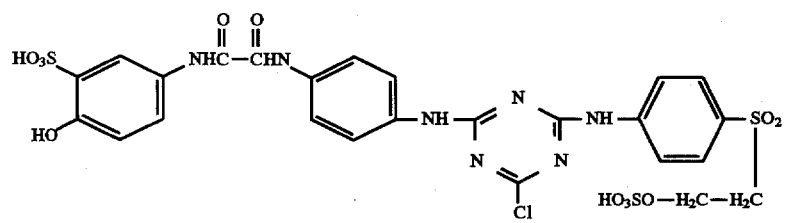

38b

EXAMPLE 39

With stirring, an aqueous solution of 5.84 parts of 4-(4'-aminobenzoylamino)benzenesulfonic acid in 40 parts water is added at room temperature to an aqueous suspension of the condensate of 3.68 parts of cyanuric chloride and 5.63 parts of 4-β-sulfatoethylsulfonylaniline (preparation as described in DE-A 3 740 650). The reaction temperature is raised to c. 30° C. and stirring is continued until the condensation is complete, while keepng the pH of the mixture constant at 6.5 by the dropwise addition of a 15% solution of sodium carbonate. The product is then salted out in conventional manner, isolated by filtration, washed with a solution of sodium chloride and dried, giving the compound of formula

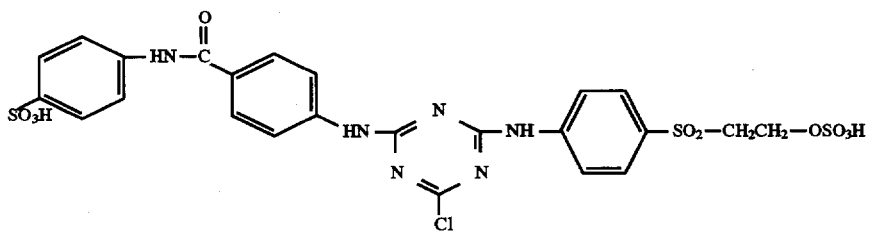

as a powder. Application of this compound to cotton fabric by a standard method of dyeing with reactive dyes gives a greatly enhanced sun protection factor compared with untreated fabric.

Application Example

In a jet dyeing apparatus, 100 g of a bleached cotton tricot fabric are treated for 20 minutes at 60° C. with a liquor containing 1 g of the compound of Example 4 and 75 g of sodium sulfate at a liquor to goods ratio of 1:15. After addition of 30 g of sodium carbonate, the cotton tricot is treated for a further 60 minutes. The fabric is then removed from the liquor, washed repeatedly with cold, warm and hot water and dried. The treated cotton tricot fabric has an excellent sun protection factor.

What is claimed is:

1. A compound of formula

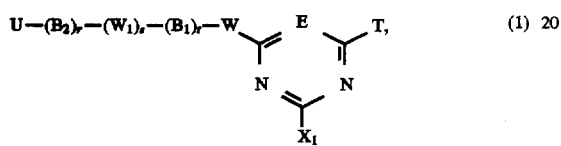   (1)

wherein $B_1$ and $B_2$ are each independently of the other an aliphatic linking group, U is the radical of formula

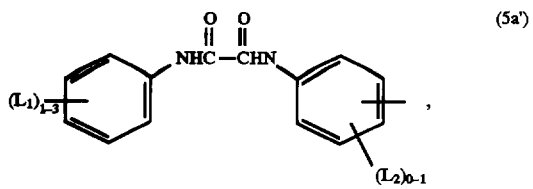   (5a')

wherein $(L_1)_{1-3}$ is 1 to 3 radicals $L_1$ selected from the group consisting of sulfo, hydroxy, $C_1$–$C_4$alkyl and $C_1$–$C_{12}$alkoxy and $(L_2)_{0-1}$ is 0 to 1 substituents $L_2$ selected from the group consisting of sulfo, $C_1$–$C_4$alkyl and $C_1$–$C_{12}$alkoxy, W is a group —$NR_2$—, —O— or —S—, $R_2$ is hydrogen or unsubstituted or substituted $C_1$–$C_4$alkyl, $W_1$ is a radical —C(O)O—, —O(O)C—, —C(O)NH— or —HN(O)C—, =E— is a group =N— or =C($T_1$)—, and $T_1$ is halogen, $C_1$–$C_4$alkylsulfonyl, formyl, $C_2$–$C_4$alkoxycarbonyl or cyano, $X_1$ is halogen, hydroxy, sulfo, $C_1$–$C_4$alkylsulfonyl, phenylsulfonyl, unsubstituted or substituted amino, 3-carboxypyridin-1-yl or 3-carbamoylpyridin-1-yl, T independently has one of the meanings given for $X_1$ or is an alkoxy, aryloxy, alkylthio or arylthio radical, or is a nitrogen-containing heterocyclic radical or is a reactive radical of formula

   (2a)

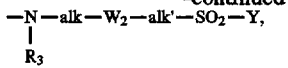   (2b)

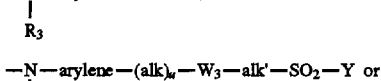   (2c)

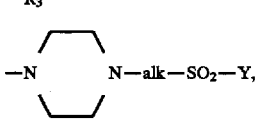   (2d)

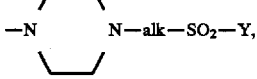   (2e)

$R_1$ is hydrogen, $C_1$–$C_4$alkyl which is unsubstituted or substituted by hydroxy, sulfo, sulfato, carboxy or cyano, or is a radical

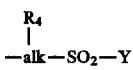

$R_3$ is hydrogen or $C_1$–$C_4$alkyl, $R_4$ is hydrogen, hydroxy, sulfo, sulfato, carboxy, cyano, halogen, $C_1$–$C_4$alkoxycarbonyl, $C_1$–$C_4$alkanoyloxy, carbamoyl or the group —$SO_2$—Y, alk and alk' are each independently of the other $C_1$–$C_6$alkylene, arylene is a phenylene or naphthylene radical which is unsubstituted or substituted by sulfo, carboxy, $C_1$–$C_4$alkyl, $C_1$–$C_4$alkoxy or halogen, Y is vinyl or a radical —$CH_2$—$CH_2$—Z and Z is a leaving group, $W_2$ is —O— or —$NR_3$—, $W_3$ is a group —$SO_2$—$NR_1$—, —$CONR_1$— or —$NR_1CO$—, and r, s, t and u are each independently of one another 0 or 1, s being 0 when t is 0, with the proviso that the compound of formula (1) carry at least one sulfo or sulfato group and at least one group which is removable under alkaline conditions.

2. A compound according to claim 1, wherein =E— is the group =N—, and r and s are each 0.

3. A compound according to claim 1, wherein $B_1$ is straight-chain or branched $C_1$–$C_6$alkylene.

4. A compound according to claim 1, wherein $X_1$ is chloro or fluoro.

5. A compound according to claim 2, wherein W is —$NR_2$— and $R_2$ is hydrogen or $C_1$–$C_4$alkyl.

6. A compound according to claim 1, wherein T is a reactive radical of formula (2a) to (2e).

7. A compound according to claim 6, wherein $W_3$ is a group of formula —CONH— or —NHCO—, $R_1$, $R_3$ and $R_4$ are each hydrogen, $W_2$ is —O— or —NH—, alk and alk' are each independently of the other ethylene or propylene, arylene is phenylene which is unsubstituted or substituted by methyl, methoxy, carboxy or sulfo, or naphthylene which is unsubstituted or substituted by sulfo, Y is vinyl or β-sulfatoethyl, and u is 0.

8. A compound according to claim 1 of formula

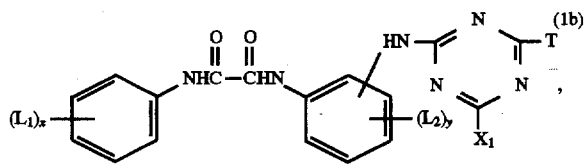

wherein $(L_1)_x$ denotes x identical or different substituents $L_1$ selected from the group consisting of sulfo, hydroxy, $C_1$–$C_4$alkyl and $C_1$–$C_{12}$alkoxy, $(L_2)_y$ denotes y substituents $L_2$ selected from the group consisting of sulfo, $C_1$–$C_4$alkyl and $C_1$–$C_{12}$alkoxy, x is 1, 2 or 3 and y is 0 or 1, $X_1$ is chloro or fluoro, and T is a fibre-reactive radical of formula

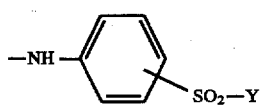

or

wherein Y is vinyl or β-sulfatoethyl.

9. A process for the preparation of a compound of formula (1) according to claim 1, which comprises reacting a compound of formula

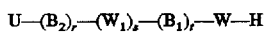

a compound of formula

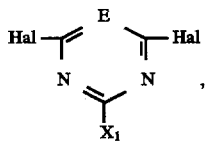

and a compound of formula $$T^*—H \quad (9)$$

wherein U, $B_1$, $B_2$, W, $W_1$, E, $X_1$, r, s and t are each as defined in claim 1, Hal is halogen, and T* has the meaning given in claim 1 for T, except halogen, with one another, in any order.

10. A process for enhancing the sun protection factor of textile fibre materials, which comprises applying one or more than one compound of formula (1) as claimed in claim 1, in an aqueous or aqueous-organic solution, to said materials, and subsequently fixing said compound or compounds thereon.

11. A process for the photochemical stabilisation of undyed, dyed or printed textile fibre materials, which comprises applying one or more than one compound of formula (1) as claimed in claim 1, in an aqueous or aqueous-organic solution, to said materials, and subsequently fixing said compound or compounds thereon.

12. A compound according to claim 1 of formula

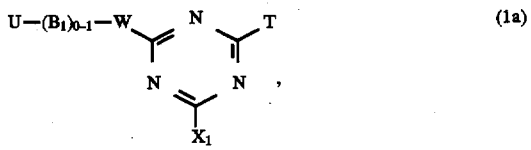

wherein $B_1$ is straight-chain or branched $C_1$–$C_6$alkylene, W is —NH—, $X_1$ is chloro or fluoro, U is a radical of formula

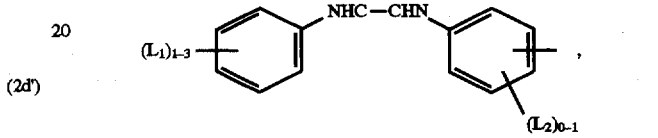

wherein $(L_1)_{1-3}$ is 1 to 3 identical or different radicals $L_1$ selected from the group consisting of sulfo, hydroxy, $C_1$–$C_4$alkyl and $C_1$–$C_{12}$alkoxy, and $(L_2)_{0-1}$ is 0 to 1 substituent $L_2$ selected from the group consisting of sulfo, $C_1$–$C_4$alkyl and $C_1$–$C_{12}$alkoxy, and T is amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, mono-, di- or trisulfonaphthylamino, morpholino or a radical of formulae (2a) to (2e) as shown in claim 1, wherein $W_3$ is a group of formula —CONH— or —NHCO—, $R_1$, $R_3$ and $R_4$ are each hydrogen, $W_2$ is —O— or —NH—, alk and alk' are each independently of the other ethylene or propylene, arylene is phenylene which is unsubstituted or substituted by methyl, methoxy, carboxy or sulfo, or naphthalene which is unsubstituted or substituted by sulfo, Y is vinyl or β-sulfatoethyl, and u is 0.

13. A compound according to claim 1, wherein the arylthio radical is a phenylthio which is unsubstituted or substituted by $C_1$–$C_4$alkyl, $C_1$–$C_4$alkoxy, halogen, hydroxy, carboxy or sulfo.

14. A process according to claim 9, wherein Hal is fluoro or chloro.

* * * * *